(12) United States Patent
Ishizaki et al.

(10) Patent No.: US 8,097,761 B2
(45) Date of Patent: Jan. 17, 2012

(54) PROCESS FOR PRODUCTION OF CAROTENOID

(75) Inventors: Tomoyuki Ishizaki, Tokyo (JP); Satoru Ishikawa, Tokyo (JP); Akira Tsubokura, Yokohama (JP); Kazuaki Hirasawa, Yokohama (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 279 days.

(21) Appl. No.: 12/294,762

(22) PCT Filed: Mar. 28, 2007

(86) PCT No.: PCT/JP2007/057518
§ 371 (c)(1),
(2), (4) Date: Sep. 26, 2008

(87) PCT Pub. No.: WO2007/114461
PCT Pub. Date: Oct. 11, 2007

(65) Prior Publication Data
US 2010/0174118 A1    Jul. 8, 2010

(30) Foreign Application Priority Data

Mar. 28, 2006 (JP) ................ 2006-087223
May 30, 2006 (JP) ................ 2006-149794

(51) Int. Cl.
    *C07C 45/00* (2006.01)
(52) U.S. Cl. ..................... 568/345; 568/367
(58) Field of Classification Search ........... 568/345, 568/367
    See application file for complete search history.

(56) References Cited

U.S. PATENT DOCUMENTS

| 5,712,110 | A  | 1/1998  | Fleno et al. |
| 6,706,278 | B1 | 3/2004  | Tsubokura et al. |
| 2002/0025548 | A1 | 2/2002 | Sibeyn et al. |
| 2003/0044495 | A1 | 3/2003 | Kagan et al. |
| 2007/0196894 | A1 | 8/2007 | Sim et al. |
| 2010/0291251 | A1 | 11/2010 | Takahashi |

FOREIGN PATENT DOCUMENTS

| EP | 0 543 023 | | 6/1992 |
| EP | 0635576 | A1 | 1/1995 |
| EP | 0670306 | | 9/1995 |
| EP | 0719866 | | 7/1996 |
| EP | 0732378 | | 9/1996 |
| EP | 1361281 | | 11/2003 |
| EP | 1 430 882 | | 12/2003 |
| EP | 2192191 | A1 | 6/2010 |
| JP | 02-049091 | A | 2/1990 |
| JP | H02-049091 | | 2/1990 |
| JP | 2-504101 | A | 11/1990 |
| JP | 5-230387 | A | 9/1993 |
| JP | 7-79796 | A | 3/1995 |
| JP | 7-304978 | A | 11/1995 |
| JP | 9-308481 | A | 12/1997 |
| JP | 10-276721 | | 10/1998 |
| JP | 11-56346 | | 3/1999 |
| JP | 11-56346 | A | 3/1999 |
| JP | 2000-515742 | A | 11/2000 |
| JP | 2001-95500 | A | 4/2001 |
| JP | 2003-144188 | | 5/2003 |
| JP | 2004-41147 | | 2/2004 |
| JP | 2004-208504 | | 7/2004 |
| JP | 2006-516293 | | 6/2006 |
| WO | 88/08025 | A1 | 10/1988 |
| WO | 01/46133 | A1 | 6/2001 |
| WO | 01/83437 | A1 | 11/2001 |
| WO | WO 02-12183 | | 2/2002 |

OTHER PUBLICATIONS

Tsubokura et al., (1999), *Int. J. Syst. Bacteriol.* 40: 277-282.
Extended European Search Report dated Mar. 28, 2011 for PCT/JP2007/057518, to which the instant U.S. Appl. No. 12/294,762 claims priority.

*Primary Examiner* — Sikarl Witherspoon
(74) *Attorney, Agent, or Firm* — McDermott Will & Emery LLP

(57) ABSTRACT

A method for producing a composition containing carotenoid at a content of 80% or greater, characterized in performing extraction on a culture of a microorganism, a concentrate of the culture, or a dried substance thereof with at least one selected from the group consisting of lower alcohols, water-containing lower alcohols, lower dialkylketones and ethers; and then washing a precipitate, obtained by concentrating the extract solution, with at least one selected from the group consisting of lower alcohols, water-containing lower alcohols, hydrocarbon-based solvents and lower dialkylketones; and food, a pharmaceutical composition or a cosmetic substance comprising the carotenoid-containing composition.

10 Claims, No Drawings

PROCESS FOR PRODUCTION OF CAROTENOID

CROSS-REFERENCE

This is a U.S. national phase application under 35 U.S.C. §371 of International Patent Application No. PCT/JP2007/057518, filed Mar. 28, 2007, and claims the benefit of Japanese Patent Application No. 2006-087223, filed Mar. 28, 2006 and Japanese Patent Application No. 2006-149794, filed May 30, 2006. The International Application was published in Japanese on Oct. 11, 2007 as WO 07/114461 A1 under PCT Article 21(2). The contents of these priority applications are incorporated into the present disclosure by reference and in their entireties.

FIELD OF THE INVENTION

The present invention relates to a method for producing carotenoid, and in particular to an industrially suitable method for producing astaxanthin usable as a component of food, pharmaceutical compositions or cosmetics. The present invention also relates to a carotenoid-containing composition obtained by such a method; and food, a pharmaceutical composition and a cosmetic substance comprising such a carotenoid-containing composition.

BACKGROUND OF THE INVENTION

Carotenoid is a natural pigment widely existent in the natural world, and is a polyene pigment having a color in the range of yellow to red or purple. Astaxanthin is one type of naturally-occurring carotenoid and exists in a free state or as an ester, or exists as various types of pigment proteins as a result of being bonded therewith.

Astaxanthin is widely used as a coloring agent for fishes and chicken's eggs. Astaxanthin is also permitted to be used as a food additive and is widely used in fat and oil processed foods, protein foods, aqueous liquid foods and the like. Astaxanthin further has an anti-oxidation activity against peroxidation of lipid excited by a free radical, a singlet oxygen erasing action which can be several hundred times stronger than that of α-tocopherol or the like, and therefore is expected to be used in functional foods, cosmetics, and pharmaceutical drugs by utilizing the strong anti-oxidation activity thereof.

Astaxanthin is distributed widely in the natural world in, for example, fishes such as salmon, trout and red sea bream, etc.; and crustaceans such as crab, shrimp, krill, etc. Astaxanthin is also produced by bacteria belonging to Agrobacterium, Brevibacterium and Paracoccus; and microorganisms including *Haematococcus pluvialis*, Phaffia yeast and the like. Carotenoid such as astaxanthin, zeaxanthin or the like is industrially produced by a chemical synthesis method, but naturally-occurring carotenoid is desired from the aspect of safety.

With such a background, many methods for producing carotenoids containing astaxanthin especially derived from algae or microorganisms which are considered to be suitable to mass production have been reported.

For example, the following method for producing carotenoid from a Haematococcus alga has been reported (Japanese Laid-Open Patent Publication No. H 11-56346). A cystocyte of a post-culture alga is treated with heated acetone to elute chlorophyll, which is a contaminant. Then, the cystocyte is spray-dried, and carotenoid is extracted from the resultant dry cells with ethanol. However, a composition obtained by such a method still contains many contaminants derived from organisms, and is not satisfactory in terms of 1) the carotenoid content, 2) the astaxanthin content, and the like.

In order to obtain a composition containing astaxanthin at a high content, the following method, for example, has been reported (Japanese Laid-Open Patent Publication No. 2002-218994). A crude xanthophylls obtained in conformity with the above-described method is acted on by lipase in the presence of water to decompose a neutral lipid, which is one contaminant. The lipase enzyme-treated liquid is decomposed into oil and water. From the separated oil layer, free fatty acid is separated from astaxanthin by distillation, and the astaxanthin is concentrated and purified. However, even after such complicated treating steps, a composition containing astaxanthin at a ratio of 30% or higher has not been obtained.

A method of obtaining astaxanthin contained at a ratio of 0.5 to 60% using a supercritical fluid extraction method (Japanese Laid-Open Patent Publication No. 2004-41147) has been reported. However, it is inevitable that an astaxanthin fraction of a content less than the targeted content is produced as a sub-product. In order to discard, or increase the astaxanthin content of, such a fraction, another concentration operation is required. Therefore, this production method is not satisfactory, in terms of the simplicity and cost, as an industrial method for producing highly pure carotenoid containing a high content of astaxanthin with little contaminants derived from organisms.

As a method using Phaffia yeast, the following method has been reported (Japanese Laid-Open Patent Publication No. H 10-276721). A crushed bacterial cell of the yeast is treated with extraction using an organic solvent, and the oil-like crude extraction obtained by concentrating the extract solution is purified by ion exchange chromatography, adsorption chromatography or the like to obtain astaxanthin. However, this method is performed by a non-industrial technique of purifying the crude solution of low concentration astaxanthin through a plurality types of column chromatography.

As another method, the following method has also been reported (Japanese Laid-Open Patent Publication No. 2004-208504). A bacterial cell after the culturing of Phaffia yeast is treated with extraction using acetone, and the resultant extract is concentrated to obtain a crude oil-like substance. A hydrocarbon-based solvent is added to this crude oil-like substance to deposit crystals. This method is highly simple, but the obtained composition contains carotenoid at a content of merely about 70 to 73% (the content of astaxanthin is merely 36 to 42%). Due to such a low content, this method is not satisfactory as a method for producing highly pure carotenoid with little contaminants derived from organisms. This method is not satisfactory also for the reason that there is a concern that acetone and the hydrocarbon-based solvent may remain in carotenoid.

As methods using E-396 strain (FERM BP-4283: deposited on Apr. 27, 1993 (date of original deposition), International Patent Organism Depositary, National Institute of Advanced Industrial Science and Technology (Central 6, Higashi 1-1-1, Tsukuba-shi, Ibaraki-ken, Japan)), which is a bacterial strain for producing astaxanthin, adonixanthin and the like, the following methods have been reported: a method of extracting by contacting a cyclic hydrophilic organic compound, which invokes a safety concern regarding the use in food production, to the bacterial cell (Japanese Laid-Open Patent Publication No. H 7-242621); and a method of using a supercritical fluid extraction method like document 3 (Japanese Laid-Open Patent Publication No. H 8-89280). A method of contacting E-396 strain to a water-soluble organic solvent, a non-polar solvent and water to perform liquid-liquid extraction (Japanese Laid-Open Patent Publication No. H 8-253695) has also been reported.

Under these circumstances, a method for industrially producing highly pure carotenoid containing astaxanthin at a high content, which is simple without requiring any special facilities or complicated operations and which uses a solvent safe for food production, is strongly desired to be established.

SUMMARY OF THE INVENTION

The present invention has an object of providing a composition containing highly pure carotenoid at a high content using a low-cost and safe solvent and a method for industrially producing the same, and also providing functional food, a pharmaceutical composition and a cosmetic substance comprising such a composition.

In order to solve the above-described problems, the present inventors conducted a research mainly on microorganism cultures. As a result, the present inventors newly found the following problems with a conventional technique of obtaining highly pure carotenoid by liquid-liquid extraction: 1) the conventional technique of attempting to realize high level purification in the state where the concentration of the solution is low is industrially inefficient because many types of solutions are needed in the purification steps; 2) it is not simple because the solvent recovery including fractionation from the mixed organic solvent is required; and 3) it is low in safety because the used solvents remain in the final product. As a result of further accumulating active studies in order to solve also these newly found problems, the present inventors found the following and completed the present invention. A highly pure carotenoid composition is obtained by performing extraction on a microorganism culture containing carotenoid, a concentrate thereof, or a dried substance thereof with a lower alcohol, and washing a precipitate, obtained by concentrating the extract solution, with a water-containing lower alcohol or a combination of a water-containing lower alcohol and a hydrocarbon-based solvent.

The present inventors also found the following and completed the present invention. A highly pure carotenoid composition is obtained by performing extraction on a microorganism culture with at least one of a lower dialkylketone and an ether, and washing a precipitate, obtained by concentrating the extract solution, with at least one of a lower alcohol and a lower dialkylketone, or with a mixed solution thereof.

In one embodiment of the present invention, a method for producing a carotenoid-containing composition follows the steps of performing extraction on a culture of a microorganism, a concentrate of the culture, or a dried substance thereof with at least one selected from the group consisting of lower alcohols, water-containing lower alcohols, lower dialkylketones and ethers; concentrating the obtained extract solution to obtain a precipitate; and washing the precipitate with at least one selected from the group consisting of lower alcohols, water-containing lower alcohols, hydrocarbon-based solvents and lower dialkylketones.

In another embodiment of the present invention, a method for producing a carotenoid-containing composition follows the steps of performing extraction on a culture of a microorganism, a concentrate of the culture, or a dried substance thereof with ethanol or acetone; concentrating the obtained extract solution to obtain a precipitate; and washing the precipitate with ethanol, water-containing ethanol or acetone.

In yet another embodiment of the present invention, a method for producing a carotenoid-containing composition follows the steps of performing extraction on a culture of a microorganism, a concentrate of the culture, or a dried substance thereof with ethanol; concentrating the obtained extract solution to obtain a precipitate; and washing the precipitate with water-containing ethanol.

(4) In still another embodiment of the present invention, a method for producing a carotenoid-containing composition follows the steps of performing extraction on a culture of a microorganism, a concentrate of the culture, or a dried substance thereof with acetone; concentrating the obtained extract solution to obtain a precipitate; and washing the precipitate with ethanol.

In yet another embodiment of the present invention, a method for producing a carotenoid-containing composition follows the steps of performing extraction on a culture of a microorganism, a concentrate of the culture, or a dried substance thereof with acetone; concentrating the obtained extract solution to obtain a precipitate; and washing the precipitate with acetone.

In another embodiment of the present invention, any of the above-described embodiments may also have the following step of further washing the precipitate with hexane.

In yet another embodiment of the present invention, the carotenoid-containing composition contains 80% or greater of carotenoid, and in still another embodiment, the carotenoid-containing composition contains 40% or greater of astaxanthin.

In another embodiment of the present invention, a DNA base sequence of the microorganism corresponding to 16S ribosomal RNA is substantially homologous to the base sequence represented by SEQ ID NO: 1.

In yet another embodiment of the present invention, the microorganism is E-396 strain (FERM BP-4283) or a mutant thereof.

In one embodiment, the present invention provides a carotenoid-containing composition obtained by the method according to any of the above-described embodiments. In another embodiment, the carotenoid-containing composition may be contained in food, a pharmaceutical composition, or a cosmetic substance.

The present invention can provide a composition containing, at a high content, naturally-occurring, highly pure, low-cost and safe carotenoid, and a method for industrially producing the same, and can also provide functional food, a pharmaceutical composition and a cosmetic substance comprising such a composition.

DETAILED DESCRIPTION OF THE INVENTION

Hereinafter, embodiments of the present invention will be specifically described. The present invention is not limited to the following description, and may be carried out in appropriate modifications other than the following illustrative embodiments without departing from the spirit of the present invention.

All the publications cited herein, for example, the prior art documents, laid-open patent publications, patent publications, and other patent-related documents, are incorporated herein in their entirety for reference.

The present invention relates to a method for producing carotenoid, characterized in performing extraction on a culture of a microorganism, etc., for example, a carotenoid-containing microorganism culture, etc. with at least one selected from the group consisting of lower alcohols, water-containing lower alcohols, lower dialkylketones and ethers; and then washing a precipitate, obtained by concentrating the extract solution, with at least one selected from the group consisting of lower alcohols, water-containing lower alcohols, hydrocarbon-based solvents and lower dialkylketones.

The method according to the present invention can provide a composition which contains astaxanthin-containing carotenoid at a content of 80% or higher, preferably 90% or higher, and which has little contaminants derived from organisms and a very small content of organic solvents other than the lower alcohols.

The microorganisms usable for the present invention include, without limitation, any microorganism capable of producing carotenoid. For example, Paracoccus bacteria, Haematococcus algae, Phaffia yeasts and the like are usable. From the viewpoint of the proliferation speed and carotenoid productivity, a bacterium, of which the DNA base sequence corresponding to 16S ribosomal RNA is substantially homologous to the base sequence represented by SEQ ID NO: 1 in the sequence listing, is preferable.

The expression "substantially homologous" means that these sequences have homology of 94% or higher, preferably 96% or higher, and more preferably 98% or higher, in consideration of the error frequency in determining the base sequence of DNA, natural mutation in microorganisms and the like. Among such bacteria, E-396 strain (FERM BP-4283) is especially preferable. It is also very preferable to use a strain highly productive of carotenoid, the strain being obtained by mutating these microorganisms for the purpose of improving the productivity of carotenoid.

The E-396 strain is deposited as international deposition to the International Patent Organism Depositary, National Institute of Advanced Industrial Science and Technology as follows:

International Deposition Authority: International Patent Organism Depositary, National Institute of Advanced Industrial Science and Technology (former National Institute of Bioscience and Human-Technology, Agency of Industrial Science and Technology, Ministry of International Trade and Industry)

Central 6, Higashi 1-1-1, Tsukuba-shi, Ibaraki-ken, 305-8566

Identification No.: E-396

Deposition No.: FERM BP-4283

Date of original deposition: Apr. 27, 1993.

There is no specific limitation on the method for producing a mutant as long as the method induces mutation. Usable methods include, for example, a chemical method using a mutating agent such as N-methyl-N'-nitro-N-nitrosoguanidine (NTG), ethylmethanesulfonate (EMS) or the like; a physical method using ultraviolet radiation, x-ray radiation or the like; or a biological method using gene recombination, transposon or the like. The mutation may be performed in one stage, or two or more stages. In the latter case, for example, a mutant of an astaxanthin-producing microorganism is obtained by the above mutation process, and then the obtained mutant is further subjected to another mutation process.

A microorganism culture, etc. usable for the present invention may be any culture, without specific limitation, which is obtained by a method capable of culturing the above-described microorganism efficiently, for example, by a method of using liquid culture, solid culture or a combination thereof using any of the following mediums.

A nutrition medium usable for culturing a microorganism used for the present invention may be any nutrition medium containing a carbon source, a nitrogen source and an inorganic salt necessary for growing a production bacterium. It may be more preferable to add a vitamin. It may be preferable to further add amino acid, nucleic acid base or the like. Other substances which may be optionally added include yeast extract, peptone, meat extract, malt extract, corn steep liquor, dry yeast, soybean cake and the like.

Usable carbon sources include sugars such as glucose, sucrose, lactose, fructose, trehalose, mannose, mannitol, maltose and the like; organic acids such as acetic acid, fumaric acid, citric acid, propionic acid, malic acid, malonic acid, pyruvic acid and the like; alcohols such as ethanol, propanol, butanol, pentanol, hexanol, isobutanol, glycerol and the like; fats and oils such as soybean oil, rice bran oil, olive oil, corn oil, sesame oil, linseed oil and the like; etc. These carbon sources may be used independently or in a combination of two or more. The ratio thereof depends on the type of the carbon source and may be appropriately adjusted, but usually is 1 to 100 g, preferably 2 to 50 g, per 1 L of the medium.

Usable nitrogen sources include, for example, potassium nitrate, ammonium nitrate, ammonium sulfate, ammonium chloride, ammonium phosphate, ammonia, urea and the like. These nitrogen sources may be used independently or in a combination of two or more. The ratio thereof depends on the type of the nitrogen source and may be appropriately adjusted, but usually is 0.1 to 30 g, preferably 1 to 10 g, per 1 L of the medium.

Usable inorganic salts include potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium carbonate, and the like. These inorganic salts may be used independently or in a combination of two or more. The ratio thereof depends on the type of the inorganic salt and may be appropriately adjusted, but usually is 0.001 to 10 g, per 1 L of the medium.

When a vitamin is added, the amount thereof depends on the type of the vitamin and may be appropriately adjusted, but usually is 0.1 to 1000 mg, preferably 1 to 100 mg, per 1 L of the medium.

The amount of each of amino acid, nucleic acid base, yeast extract, peptone, meat extract, malt extract, corn steep liquor, dry yeast, soybean cake and the like depends on the type of the substance and may be appropriately adjusted, but usually is 0.2 g to 200 g, preferably 3 to 100 g, per 1 L of the medium.

The pH of the medium is adjusted to 2 to 12, preferably 6 to 9. The culturing is performed at a temperature of 15 to 80° C., preferably 20 to 35° C., for 1 to 20 days, preferably 2 to 8 days, under an aerobic condition. The aerobic condition is, for example, shaking culture, aeration and stirring culture, or the like.

A preferable method for extracting astaxanthin produced by a cultured microorganism used for the present invention is as follows. After the culture, the culture solution is treated with concentration by membrane filtration to obtain a bacterial cell concentrated solution, or is treated with centrifugation, pressurization, filtration at reduced pressure, or any other generally known filtration method to obtain a wet bacterial cell. The bacterial cell concentrated solution or the wet bacterial cell is treated with atomization drying, fluidized drying, rotating drum drying, lyophilization or any other generally known drying method to obtain a dry bacterial cell. The dry bacterial cell is treated with extraction by the following method. It is also recommended that before performing the following extraction, the culture solution, the bacterial cell concentrated solution, the wet bacterial cell or the dry bacterial cell is treated with one, or at least two, of a chemical treatment using an alkaline reagent, a surfactant or the like; a biochemical treatment using a bacteriolytic enzyme, a lipid decomposing enzyme, a proteolytic enzyme or the like; and a physical treatment using ultrasonic waves, pulverization or the like. The dry bacterial cell is usually considered to contain astaxanthin at a ratio of about 20 mg/g.

A solvent usable for extraction from a cultured microorganism (a culture of a microorganism), a concentrate of the culture or a dried substance thereof (herein, also referred to as "cultured microorganism, etc." or "microorganism culture, etc.") used for the present invention (hereinafter, such a solvent may be referred to as an "extraction solvent") may be any one selected from the group consisting of lower alcohols, lower dialkylketones and ethers, or a combination of thereof.

Among the lower alcohols, methanol, ethanol, n-propanol or isopropanol are preferable, ethanol and isopropanol are more preferable, and ethanol is especially preferable.

The temperature of the solvent for extraction is preferably 0° C. to the boiling point of the used solvent, and is more preferably around a temperature which is lower than the boiling point of the used solvent by about 20° C. For ethanol, 25° C. to 60° C. is preferable, 40° C. to 55° C. is more preferable, and 45° C. to 52° C. is still more preferable. The amount of the extraction solvent may be any amount with which the amount of astaxanthin contained in the bacterial cell can be dissolved. For example, in the case of extraction from a dry bacterial cell with ethanol, the amount is 1 to 90 kg, preferably 6 to 20 kg, per 1 g of astaxanthin contained in the bacterial cell.

For example, when extraction is performed with ethanol at 50° C. from 1 g of dry bacterial cell, containing about 20 mg of astaxanthin, obtained from a cultured microorganism, etc. mentioned above used for the present invention, the amount of ethanol may be about 70 g to 1800 g, preferably about 150 g to 700 g, and more preferably about 250 g to 500 g.

Among the lower dialkylketones and ethers usable as the extraction solvent, for example, acetone, methylethylketone and tetrahydrofuran are preferable, acetone and tetrahydrofuran are more preferable, and acetone is especially preferable.

The temperature of the solvent for extraction is, like above, preferably 0° C. to the boiling point of the used solvent, and is more preferably around a temperature which is lower than the boiling point of the used solvent by about 5° C. For acetone, 25° C. to 55° C. is preferable, 40° C. to 55° C. is more preferable, and 45° C. to 52° C. is still more preferable. The amount of the extraction solvent may be any amount with which the amount of astaxanthin contained in the bacterial cell can be dissolved. For example, in the case of extraction from a dry bacterial cell with acetone, the amount is 0.2 to 18 kg, preferably 0.9 to 3 kg, per 1 g of astaxanthin contained in the bacterial cell.

For example, when extraction is performed with acetone at 50° C. from 1 g of dry bacterial cell, containing about 20 mg of astaxanthin, obtained from a cultured microorganism, etc. mentioned above used for the present invention, the amount of acetone may be about 7 g to 180 g, preferably about 15 g to 70 g, and more preferably about 25 g to 50 g.

When it is desired to suppress oxidation of carotenoid during the extraction operation to a minimum possible level, the extraction may be performed under an atmosphere of an inert gas such as nitrogen gas, or an antioxidant used for pharmaceutical drugs or foods may be appropriately selected and added to the extraction solvent. These treatments may be combined.

It is preferable that the antioxidant is removed from the carotenoid composition in the end, but removal may not be necessary depending on the type of the antioxidant used.

It is not necessary to limit the extraction time. When extraction is performed at room temperature or higher, a shorter time is preferable in order to minimize the yield decrease caused by thermal decomposition. For example, for extraction with ethanol at 50° C., within 12 hours is preferable, within 8 hours is more preferable, within 6 hours is still more preferable, within 4 hours is especially preferable, and within 3 hours is most preferable. For extraction with acetone at 50° C., within 12 hours is preferable, within 6 hours is more preferable, within 3 hours is still more preferable, within 2 hours is especially preferable, and within 1 hour is most preferable.

Methods for concentrating the extract solution obtained by extraction from a microorganism culture, etc. with a lower alcohol include heating and/or concentration at reduced pressure. When it is desired to suppress oxidation of carotenoid during the concentration to a minimum possible level, the concentration may be performed under an atmosphere of an inert gas such as nitrogen gas. The degree of concentration may be appropriately determined in consideration of the amount and the purity of the precipitate to be obtained. For example, the extract solution may be concentrated 10- to 1000-fold, preferably 30- to 500-fold, more preferably 50- to 400-fold, and especially preferably 100- to 200-fold, with respect to the weight thereof.

Methods for concentrating the extract solution obtained by extraction from a cultured microorganism, etc. with at least one of a lower dialkylketone and an ether include heating and/or concentration at reduced pressure like above. When it is desired to suppress oxidation of carotenoid during the concentration to a minimum possible level, the concentration may be performed under an atmosphere of an inert gas such as nitrogen gas. The degree of concentration may be appropriately determined in consideration of the amount and the purity of the precipitate to be obtained. For example, the extract solution may be concentrated 3- to 100-fold, preferably 7- to 50-fold, more preferably 15- to 40-fold, and especially preferably 20- to 30-fold, with respect to the weight thereof.

The solution removed by concentrating the extract solution may be reused for extraction from a cultured microorganism, etc. with no further treatment.

The concentrated solution obtained by the concentration may be appropriately cooled in consideration of the amount and the purity of the precipitate to be obtained so as to further promote the precipitation. The cooling temperature is, for example, a temperature which is lower than the temperature at the time of extraction by 20° C. or greater, or is 5° C., 0° C., −5° C., −10° C. or the like. Alternatively, in some embodiments, it is more preferable that the precipitate is obtained by stopping the concentration immediately before the precipitate is generated, and then appropriately cooling the concentrated solution in consideration of the amount and the purity of the precipitate to be obtained. The cooling temperature is the same as above. In this case, a seed precipitate (a substance acting as a seed for causing precipitation; for example, a carotenoid solid such as a carotenoid crystal or the like) may be added in order to smoothly generate the precipitate.

The precipitate is collected by a filtration device of a decompression or compression type, a centrifuge or the like. In this process, the collected precipitate may be optionally washed using a small amount of the same solvent as the extraction solvent. When it is desired to suppress oxidation of carotenoid to a minimum possible level, the operation may be performed under an atmosphere of an inert gas such as nitrogen gas. Considering that the washing solvent is recovered and reused a plurality of times for precipitate washing, which is performed to realize high level purification in a later stage, it is preferable to provide some means for collecting the precipitate under such a condition that the solvent used for the extraction remains in the precipitate at a minimum possible level.

It is also possible to recover the solvent from the filtrate containing organism-derived contaminants which are generated when the precipitate is collected, using a method of distillation or of removal by distillation at reduced pressure, so that the solvent can be reused for extraction from a cultured microorganism, etc. and precipitate washing.

Regarding the process of washing of the resultant precipitate to obtain highly pure carotenoid, the undried substance may be washed with no further treatment, or washed after being dried. The precipitate does not absolutely need to be pulverized, but may be pulverized before being washed in order to improve the washing efficiency or may be pulverized during the washing. For the washing, it is important to use the following solvents. Specific washing conditions may be appropriately determined in accordance with the purity of the obtained precipitate.

The solvent used for the washing may be one of lower alcohols, water-containing lower alcohols, hydrocarbon-based solvents, lower dialkylketones, or a combination thereof.

According to the method of the present invention, in the case where the extraction is performed from a microorganism culture, etc. with a lower alcohol, a preferable solvent used in the washing step is a water-containing lower alcohol, or a combination of a water-containing lower alcohol and a hydrocarbon-based solvent. In the case where the extraction is performed from a microorganism culture, etc. with at least one of a lower dialkylketone and an ether, it is preferable to wash the precipitate, obtained by concentrating the extract solution, with a lower alcohol (e.g., a solvent containing an alcohol having a carbon number of 1 to 3) or a lower dialkylketone (e.g., a solvent containing a ketone having a carbon number of 3 to 6).

Usable lower alcohols include alcohols having a carbon number of 1 to 3 including methanol, ethanol, n-propanol, isopropanol and the like. Ethanol and isopropanol are preferable, and ethanol is especially preferable. When a water-containing lower alcohol is used, the water content in the lower alcohol is preferably 5 to 95%, more preferably 10 to 50% and especially preferably 20 to 40%.

Usable lower dialkylketones include ketones having a carbon number of 3 to 6 including acetone, methylethylketone, diethylketone, methylisobutylketone and the like. Acetone and methylethylketone are preferable, and acetone is especially preferable.

In one preferable embodiment, the washing may be performed with a mixed solvent also containing water or any other organic solvent to such a degree that the washing capability is not decreased.

According to the present invention, the precipitate obtained by the washing step may be further washed with a hydrocarbon-based solvent.

Usable hydrocarbons include alkyls having a carbon number of 5 to 7 including pentane, hexane, cyclohexane, heptane and the like. Hexane and heptane are preferable, and hexane is especially preferable.

According to the present invention, a "combination of a water-containing lower alcohol and a hydrocarbon-based solvent" refers to using a water-containing lower alcohol (e.g., water-containing ethanol) and a hydrocarbon-based solvent (e.g., hexane), in a mixed state, or washing with a water-containing lower alcohol (e.g., water-containing ethanol) and then washing with a hydrocarbon-based solvent (e.g., hexane). From the viewpoint of the washing efficiency, the latter is preferable.

In one preferable embodiment, the washing may be performed with a mixed solvent also containing water or any other organic solvent to such a degree that the washing capability is not decreased. In this case, however, it is necessary to consider the amount of such an organic solvent remaining in the resultant carotenoid-containing composition.

For the lower limit of the amount of the solvent used for the washing, it is preferable to select a minimum possible amount which is industrially acceptable in consideration of the purity of the precipitate. For example, when 25%-water-containing ethanol is used, the amount is acceptably twice or greater, preferably 4 times or greater, more preferably 6 times or greater, still more preferably 10 times or greater, and may be even 20 times or greater when necessary, with respect to the following weight: when a dried precipitate is washed, with respect to the weight thereof; and when an undried precipitate is washed, with respect to the weight in a dried state, which is calculated using a conversion coefficient that can be set by checking, before drying, the correlation between the volume or weight of the undried precipitate and that of the dried precipitate.

The upper limit may be 200 times at the maximum. Especially from the viewpoint of the industrial efficiency, the upper limit is preferably 100 times or less, more preferably 80 times or less, still more preferably 40 times or less, may be 20 times or less if the conditions are set in detail, and may be even 10 times or less in some cases.

When, for example, hexane or acetone is used for the washing, the amount thereof is acceptably 30 times or greater, preferably 35 times or greater, more preferably times or greater, and may be even 40 times or greater when necessary, with respect to the following weight: when a dried precipitate is washed, with respect to the weight thereof; and when an undried precipitate is washed, with respect to the weight in a dried state, which is calculated using a conversion coefficient that can be set by checking, before drying, the correlation between the volume or weight of the undried precipitate and that of the dried precipitate. The upper limit may be 200 times at the maximum. Especially from the viewpoint of the industrial efficiency, the upper limit is preferably 100 times or less, more preferably 80 times or less, still more preferably 60 times or less, and may be even about 50 times or less if the conditions are set in detail.

There is no specific limitation on the washing method. Practically preferable methods include, for example, a method of performing filtration after the suspension is stirred, a method of passing the solution from above the precipitate, and the like. The temperature at the time of washing is preferably 1° C. to 30° C. in general, but may be 1° C. or lower or 30° C. or higher depending on the situation. The upper limit of the temperature may be around the boiling point of the solvent used for the washing (for example, 78° C. for ethanol, 56° C. for acetone). When it is desired to suppress oxidation of carotenoid to a minimum possible level, the washing may be performed under an atmosphere of an inert gas such as nitrogen gas.

It is further possible to recover the solvent from the waste fluid which is generated during the washing performed to obtain highly pure carotenoid from the precipitate, using a method of distillation or of removal by distillation at reduced pressure, so that the obtained solvent can be reused for another washing step.

It is also very preferable to optionally add a step of washing with water substituted for the solvent, at the end of the washing, in order to reduce the amount of the solvent remaining in the carotenoid-containing composition according to the present invention after the washing and drying. For example, it is preferable to add a final step of washing with a small amount of low temperature water or ethanol.

In order to maximize the yield amount of carotenoid and the main components such as astaxanthin and the like in the carotenoid-containing composition obtained by the above-described method, the conditions of the above-described purification steps (e.g., the type of the extraction solvent or the washing solution) may be appropriately adjusted.

The content of carotenoid in the carotenoid-containing composition according to the present invention is preferably 80% or greater, more preferably 85% or greater, still more preferably 90% or greater, further more preferably 91% or greater, further more preferably 95% or greater, especially preferably 97% or greater, and most preferably 98% or greater. The content of astaxanthin in the carotenoid is preferably 40% or greater, more preferably 45% or greater, still more preferably 46% or greater, especially preferably 47% or greater, further more preferably 50% or greater, especially preferably 55% or greater, and most preferably 60% or greater.

Specifically, for example, a composition containing carotenoid at a content of 95% or greater is obtained by performing extraction on a microorganism culture, etc. with acetone, and then washing the precipitate, obtained by concentrating the extract solution, with ethanol. A composition containing carotenoid at a content of 90% or greater is obtained by performing extraction on a microorganism culture, etc. with acetone, and then washing the precipitate, obtained by concentrating the extract solution, with acetone.

As described above, a production method according to the present invention is characterized in performing extraction on a microorganism culture, etc. with at least one selected from the group consisting of lower alcohols, lower dialkylketones and ethers, and then washing the precipitate, obtained by concentrating the extract solution, with a lower alcohol, a hydrocarbon-based solvent or a combination thereof.

Carotenoid can be obtained at a high level of purity only by these very simple operations.

The method according to the present invention is significantly industrially advantageous over the conventional art on the points of 1) not requiring a complicated operation and 2) not requiring an inefficient purity improving operation performed in the state where the concentration of the solution is as low as 1% or less, which is required in column purification or liquid-liquid extraction. The present invention has an meritorious effect of realizing a superior industrial production method on the points of 3) providing a highly pure carotenoid composition, containing astaxanthin at a high content and not containing any halogen-based organic solvent, at low cost and 4) being capable of easily recovering the solvent used in each step.

Foods, pharmaceutical compositions, and cosmetic substances comprising a carotenoid-containing composition according to the present invention are encompassed in the present invention.

Pharmaceutical drugs comprising highly pure carotenoid containing astaxanthin at a high content produced by a production method according to the present invention are available in formulations including powder, granule, pill, soft capsule, hard capsule, tablet, chewable tablet, disintegrating tablet, syrup, liquid medicine, suspension, suppository, ointment, cream, gel, sticky medicine, inhalant, injection and the like. These formulations are prepared in accordance with a usual method. Carotenoid is not highly soluble in water, and so is used as being dissolved in a non-hydrophilic organic solvent such as a vegetable oil, an animal oil or the like, or as being dispersed or emulsified in an aqueous solution together with an emulsifier, a dispersant, a surfactant or the like using a homogenizer (high pressure homogenizer). In order to improve the capability of carotenoid of being absorbed, carotenoid may be used after being pulverized to an average particle diameter as small as about 1 micrometer.

Additives usable for producing the formulations include, for example, animal and vegetable oils including soybean oil, saffron oil, olive oil, germ oil, sunflower oil, beef tallow, sardine oil and the like; polyhydric alcohols including polyethylene glycol, propylene glycol, glycerin, sorbitol and the like; surfactants including sorbitan fatty acid ester, sucrose fatty acid ester, glycerin fatty acid ester, polyglycerin fatty acid ester and the like; excipients including purified water, lactose, starch, crystalline cellulose, D-mannitol, lecithin, gum arabic, sorbitol solution, sugar solution and the like; sweeteners, coloring agents, pH adjusters, flavor substances, etc. A liquid formulation may be dissolved or suspended in water or any other appropriate medium when being administered. A tablet or a granule may be coated by a well known method.

Administration by injection is preferably performed intravenously, intraperitoneally, intramuscularly, subcutaneously, percutaneously, intra-articularly, in synovial bursa, in bulla, in periosteum, sublingually, orally or the like, and is especially preferably performed intravenously or intraperitoneally. The intravenous administration may be drip administration or porous administration.

When carotenoid is used as a pharmaceutical drug, the daily dose for an adult is 1 mg to 3 g, preferably 3 mg to 1 g, and more preferably 10 mg to 670 mg. When converted to an amount per 1 kg of the body weight, such doses are respectively, 17 µg to 50 mg, 54 µg to 17 mg, and 160 µg to 12 mg. Such a dose is administered once a day or as being divided to several times a day. The pharmaceutical effective amount, administration method, administration means and administration period can be appropriately set by a person of ordinary skill in the art in accordance with the clinical state, gender, age, body weight or the like of each administration target.

Foods comprising highly pure carotenoid containing astaxanthin at a high content according to the present invention are available as, for example, supplements (powder, granule, soft capsule, hard capsule, tablet, chewable tablet, disintegrating tablet, syrup, liquid medicine, etc.), drinks (tea, carbonated drink, lactic drink, sports drink, etc.), confectionaries (gummi, jelly, chewing gum, chocolate, cookie, candy, etc.), oils, fats and oils foods (mayonnaise, dressing, butter, cream, margarine, etc.), seasonings (ketchup, sauce, etc.), liquid foods, dairy products (milk, yoghurt, cheese, etc.), breads, noodles (udon, soba, ramen, pasta, fried noodle, kishimen, somen, hiyamugi, bihon, etc.), and the like.

Functional foods comprising highly pure carotenoid containing astaxanthin at a high content according to the present invention may optionally contain any of various nutrients, various vitamins (vitamin A, vitamin B1, vitamin B2, vitamin B6, vitamin C, vitamin E, etc.), various minerals, dietary fiber, polyunsaturated fatty acid, other nutrients (coenzyme Q10, carnitine, sesamine, α-lipoic acid, inositol, D-chiroinositol, pinitol, phosphatidylserine, phosphatidyl DHA, phosphatidyl inositol, taurine, glucosamine, chondroitin sulfate, S-adnosylmethionine, etc.), stabilizers such as, for example, dispersants and emulsifiers, sweeteners, taste enriching components (citric acid, malic acid, etc.), flavor substances, royal jelly, propolis, agaricus, and the like. Herbs such as peppermint, bergamot, chamomile, lavender and the like can be also contained. Elements such as theanine, dehydroepiandosteron, melatonin and the like can be also contained.

Cosmetic products comprising highly pure carotenoid containing astaxanthin at a high content according to the present invention include cream, milky lotion, lotion, micro-emulsion essence, bathwater additive and the like, and may contain aromatic essence or the like.

When carotenoid is used as food or a supplement, there is no specific limitation on the dose or administration manner. The dose may be 17 µg to 50 mg, preferably 54 µg to 17 mg, and more preferably 160 µg to 12 mg, when converted to the dose per 1 kg of the body weight.

When carotenoid is used as a cosmetic substance, the dose is 10 µg to 5 g, preferably 10 µg to 2 g, and more preferably 10 µg to 1 g, per 100 g of the cosmetic substance.

EXAMPLES

The present invention will be described by way of examples, a reference example, formulation examples and test examples. The scope of the present invention is not limited to the following examples.

In the examples and comparative examples, astaxanthin and carotenoid were quantized by high performance liquid chromatography (HPLC). Two columns of Wakosil-II 5 SIL-100 (φ4.6×250 mm) (produced by Wako Pure Chemical Industries, Ltd.) were connected to each other to be used as a column Elution was performed by flowing an n-hexane-tetrahydrofuran-methanol mixed solution (40:20:1), which was a mobile phase, at a flow rate of 1.0 ml/min at a constant temperature around room temperature. The measurement was performed as follows. The sample was dissolved in tetrahydrofuran, and the resultant substance was diluted 100-fold with the moving phase. 20 µL of the resultant solution was injected. The column elution solution was detected at a wavelength of 470 nm. As the reference product for quantification, astaxanthin produced by Sigma (Cat. No. A9335) was used. The astaxanthin concentration of the reference solution was set using the following expression after measuring the absorbance of the reference solution of 477 nm (A) and the area percentage % (B) of the astaxanthin peak at the time of HPLC analysis under the above-described conditions.

$$\text{Astaxanthin concentration(mg/L)} = A \div 2150 \times B \times 100$$

Example 1

Production of Highly Pure Carotenoid Containing Astaxanthin at a High Content—1

Step 1: Step of Culturing E-396 Strain 10 ml of a medium having a composition of 2 g/L of glucose, 3 g/L of meat extract, 10 g/L of peptone, and 5 g/L of sodium chloride was put into test tubes having a diameter of 18 mm, and sterilized with vapor at 121° C. for 15 minutes. One platinum loop of E-396 strain (FERM BP-4283) was inoculated in the resultant substance and subjected to two-way shaking culture at 30° C. for 6 days at 300 rpm. The resultant culture solution in 200 test tubes (2 L) was centrifuged and then lyophilized to obtain dry bacterial cells containing astaxanthin at a ratio of 16 mg/g.

Step 2: Step of Extracting with Ethanol

To 62 g of the dry bacterial cells obtained in step 1 of this example, 18 kg of ethanol was added, and while stirring the resultant substance at 50° C. for 3 hours, carotenoid containing astaxanthin was extracted. Next, the bacterial cells were removed by filtration, and the bacterial cell cake was washed with ethanol to obtain 18 kg of extract solution containing 0.0028% (wt./wt.) of astaxanthin and having a carotenoid weight concentration of 0.0050% (wt./wt.).

Step 3: Step of Concentrating the Extract Solution, and Depositing 18 kg of the extract solution obtained in step 2 of this example was concentrated at reduced pressure using an evaporator to obtain a concentrated solution (about 80 g) containing a precipitate and also a removed solution (about 17 kg of ethanol). The concentrated solution was stirred while being cooled at an ambient temperature of 5° C. for 1 hour.

Step 4: Step of Filtrating the Precipitate, and Drying

About 80 g of the cooled concentrated solution obtained in step 3 of this example was filtrated at reduced pressure to obtain a precipitate cake containing carotenoid. 20 g of ethanol was added onto the cake, and the resultant substance was filtrated and washed, and then dried at reduced pressure at 35° C. overnight to obtain 1.5 g of dried precipitate. The contents of astaxanthin and carotenoid in this dried substance were 38% and 64%, respectively.

Step 5: Step of Washing with 25%-Water-Containing Ethanol and Hexane, and Drying To 1.5 g of the dried substance precipitate obtained in step 4 of this example, 100 g of 25%-water-containing ethanol was added, and the resultant substance was stirred and washed at room temperature for 1 hour in the state where carotenoid corresponding to 0.96% was suspended. The resultant washed substance was sampled by filtration at reduced pressure and dried at reduced pressure at 35° C. overnight to obtain 1.02 g of dried substance washed with 25%-water-containing ethanol. The contents of astaxanthin and carotenoid in this dried substance washed with 25%-water-containing ethanol were 52% and 88%, respectively.

Next, to the obtained 1.02 g of the dried substance washed with 25%-water-containing ethanol, 80 g of hexane was added, and the resultant substance was stirred and washed at room temperature for 1 hour in the state where carotenoid corresponding to 1.1% was suspended. The resultant washed substance was sampled by filtration at reduced pressure and dried at reduced pressure at 35° C. overnight to obtain 0.88 g of dried substance washed with hexane. The contents of astaxanthin and carotenoid in this dried substance washed with hexane were 56% and 94%, respectively.

Step 6: Step of Recovering the Solvents by Distillation at Reduced Pressure

About 100 g (about 120 mL) of filtrate generated in step 4 was distilled at reduced pressure to recover 80 g of ethanol to the removed solution side. About 80 g (about 118 mL) of hexane filtrate generated in step 5 was distilled at reduced pressure to recover 74 g of hexane to the removed solution side.

Example 2

Production of Highly Pure Carotenoid Containing Astaxanthin at a High Content using the Recovered Solvents—1

To 31 g of the dry bacterial cells obtained in step 1 of Example 1, 9 kg of the removed solution (ethanol) obtained in step 3 of Example 1 was added, and the resultant substance was treated with extraction of carotenoid and filtration of the bacterial cells in conformity with step 2 of Example 1 to obtain 9 kg of extract solution. The extract solution was concentrated at reduced pressure in conformity with step 3 of Example 1 to obtain about 40 g of cooled concentrated solution. The cooled concentrated solution was treated in conformity with step 4 of Example 1 to obtain a precipitate by filtration. Next, 10 g of the ethanol recovered in step 6 of Example 1 was added onto the precipitate cake, and the resultant substance was filtrated and washed, and then dried to obtain 0.75 g of dried substance. To this dried substance, 25%-water-containing ethanol produced by mixing 37.5 g of the ethanol recovered in step 6 of Example 1 and 12.5 g of water was added, and the resultant substance was treated in conformity with step 5 of Example 1 to obtain 0.51 g of dried substance washed with 25%-water-containing ethanol. To the obtained dried substance washed with 25%-water-containing ethanol, 40 g of the hexane recovered in step 6 of Example 1 was added, and the resultant substance was washed and dried in conformity with step 5 of Example 1 to obtain 0.44 g of dried substance washed with hexane. Whereas the contents of astaxanthin and carotenoid in the substance dried at reduced pressure but before being washed with 25%-water-containing ethanol and hexane were respectively 38% and 64%, the contents of astaxanthin and carotenoid in the dried substance washed with 25%-water-containing ethanol and hexane were respectively 56% and 94%.

From the above, it was confirmed that reuse of the recovered solvents presents no problem.

Example 3

Production of Highly Pure Carotenoid Containing Astaxanthin at a High Content—2

The steps of bacteria culturing, extraction, and concentration and deposit were performed as in steps 1 through 3 of Example 1, and about 80 g of the cooled concentrated solution obtained in step 3 was filtrated at reduced pressure in conformity with step 4 of Example 1 to obtain a precipitate cake containing carotenoid. 20 g of ethanol was added onto the cake, and the resultant substance was filtrated and washed. Then, a part of the cake was sampled in order to check the content of carotenoid in the precipitate. The step of drying was omitted. Then, 100 g of 25%-water-containing ethanol was added onto the cake, and the resultant substance was further filtrated and washed. The cake obtained by the filtration and washing was dried at reduced pressure at 35° C. overnight to obtain 1.5 g of dried substance washed with 25%-water-containing ethanol. Whereas the contents of astaxanthin and carotenoid in the substance dried at reduced pressure but before being washed with 25%-water-containing ethanol were respectively 38% and 64%, the contents of astaxanthin and carotenoid in the dried substance washed with 25%-water-containing ethanol were respectively 52% and 88%.

From about 100 g (about 120 mL) of filtrate obtained by filtration of the precipitate performed in conformity with step 4 of Example 1, 85 g of ethanol was recovered.

Example 4

Production of Highly Pure Carotenoid Containing Astaxanthin at a High Content using the Recovered Solvent—2

To 31 g of the dry bacterial cells used in Example 3, 9 kg of the removed solution (ethanol) obtained in Example 3 was added, and the resultant substance was treated with extraction of carotenoid and filtration of the bacterial cells in conformity with step 2 of Example 1 to obtain 9 kg of extract solution. The extract solution was concentrated at reduced pressure in conformity with step 3 of Example 1 to obtain about 40 g of cooled concentrated solution. The cooled concentrated solution was treated in conformity with step 4 of Example 1 to obtain a precipitate by filtration. The step of drying was omitted as in Example 3. Then, 50 g of 25%-water-containing ethanol produced by mixing 37.5 g of the ethanol recovered in Example 3 and 12.5 g of water was added onto the precipitate cake, and the resultant substance was filtrated and washed. The cake obtained by the filtration and washing was dried at reduced pressure at 35° C. overnight to obtain 0.58 g of dried substance washed with 25%-water-containing ethanol. Whereas the contents of astaxanthin and carotenoid in the substance dried at reduced pressure but before being washed with 25%-water-containing ethanol were respectively 38% and 64%, the contents of astaxanthin and carotenoid in the dried substance washed with 25%-water-containing ethanol were respectively 52% and 88%.

From the above, it was confirmed that even when the ethanol recovered by distillation at reduced pressure in Example 4 is used, no reduction in the washing capability is recognized.

Food Example 1

Margarine

The astaxanthin composition obtained in Example 1 was added as an antioxidant and coloring agent to vegetable oil such that the astaxanthin composition would be contained at 5% by weight of margarine. The resultant substance was stirred together with an emulsifier and the like so as to be uniform, and margarine was produced by a usual method. As compared with usual margarine, the obtained margarine exhibited a pale red color because of the presence of astaxanthin.

Food Example 2

Artificial Salmon Roe

The astaxanthin composition obtained in Example 1 was added to a 1% aqueous solution of sodium alginate at a ratio of 0.6%, and dispersed by a homogenizer. The resultant substance was dropped to a 5% aqueous solution of calcium chloride as a coagulator and molded into spheres having a diameter of 5 mm The spheres had a close-to-natural external appearance, and were very similar to salmon roe in terms of the shape, color and taste.

Formulation Example 1

Astaxanthin-Containing Tablet

To 120 parts by weight of the carotenoid-containing composition obtained in Example 1, 330 parts by weight of crystalline cellulose, 15 parts by weight of carmellose-calcium, 10 parts by weight of hydroxypropyl cellulose and 60 parts by weight of purified water were mixed in a usual method, and the resultant substance was dried. Then, 10 parts by weight of magnesium stearate was added thereto, and the resultant substance was tableted to obtain 100 mg of tablets containing a carotenoid-containing composition at a ratio of 20 mg/piece.

Formulation Example 2

Astaxanthin-Containing Soft Capsule

One part by weight of the carotenoid-containing composition obtained in Example 1 was suspended in soybean oil of a part by weight 5 times larger, and the resultant substance was sufficiently mixed so as to be uniform. Then, the resultant substance was filled into capsules by a capsule filler to obtain reddish brown capsules each containing 300 mg.

Cosmetic Example

Astaxanthin-Containing Cream (Cosmetic Substance)

The astaxanthin-containing composition obtained in Example 1 was added to white petrolatum so as to be contained at a ratio of 10% by weight, and the resultant substance was stirred together with an aromatic and the like so as to be uniform. Then, cream was produced by a usual method.

Example 5

Production of Highly Pure Carotenoid Containing Astaxanthin at a High Content—3

Step 1: Step of Culturing E-396 Strain 10 ml of a medium having a composition of 2 g/L of glucose, 3 g/L of meat extract, 10 g/L of peptone, and 5 g/L of sodium chloride was put into test tubes having a diameter of 18 mm, and sterilized with vapor at 121° C. for 15 minutes. One platinum loop of E-396 strain (FERM BP-4283) was inoculated in the resultant substance and subjected to two-way shaking culture at 30° C. for 6 days at 300 rpm. The resultant culture solution in 200 test tubes (2 L) was centrifuged and then lyophilized to obtain dry bacterial cells containing astaxanthin at a ratio of 16 mg/g.

Step 2: Step of Extracting with Acetone

To 50 g of the dry bacterial cells obtained in step 1 of this example, 2.2 kg of acetone was added, and while stirring the resultant substance at 50° C. for 1 hour, carotenoid containing astaxanthin was extracted. Next, the bacterial cells were removed by filtration, and the bacterial cell cake was washed with acetone to obtain 2.3 kg of extract solution containing 0.0034% (wt./wt.) of astaxanthin and having a carotenoid weight concentration of 0.077% (wt./wt.).

Step 3: Step of Concentrating the Extract Solution, and Depositing 2.3 kg of the extract solution obtained in step 2 of this example was concentrated at reduced pressure using an evaporator to obtain a concentrated solution (about 80 g) containing a precipitate and also a removed solution (about 2 kg of acetone). The concentrated solution was stirred while being cooled at an ambient temperature of 5° C. for 1 hour.

Step 4: Step of Filtrating the Precipitate, and Drying

About 80 g of the cooled concentrated solution obtained in step 3 of this example was filtrated at reduced pressure to obtain a precipitate cake containing carotenoid. 20 g of acetone was added onto the cake, and the resultant substance was filtrated and washed, and then dried at reduced pressure at 35° C. overnight to obtain 2.13 g of dried precipitate. The contents of astaxanthin and carotenoid in this dried substance were 34% and 71%, respectively.

Step 5: Step of Washing with Ethanol, and Drying

To 2.13 g of the dried precipitate obtained in step 4 of this example, 80 g of ethanol was added, and the resultant precipitate was stirred and washed at room temperature for 1 hour in the state where carotenoid corresponding to 1.8% was suspended. The resultant washed substance was sampled by filtration at reduced pressure and dried at reduced pressure at 35° C. overnight to obtain 1.49 g of dried substance washed with ethanol. The contents of astaxanthin and carotenoid in this dried substance washed with ethanol were 47% and 98%, respectively.

Step 6: Step of Recovering the Solvents by Distillation at Reduced Pressure

About 100 g (about 120 mL) of filtrate generated in step 4 was distilled at reduced pressure to recover 80 g of acetone to the removed solution side. About 80 g (about 100 mL) of filtrate generated in step 5 was distilled at reduced pressure to recover 76 g of ethanol to the removed solution side.

Example 6

Production of Highly Pure Carotenoid Containing Astaxanthin at a High Content using the Recovered Solvent—3

To 25 g of the dry bacterial cells obtained in step 1 of Example 5, 1.1 kg of the removed solution (acetone) obtained in step 3 of Example 5 was added, and the resultant substance was treated with extraction of carotenoid and filtration of the bacterial cells in conformity with step 2 of Example 5 to obtain 1.2 kg of extract solution. The extract solution was concentrated at reduced pressure in conformity with step 3 of Example 5 to obtain about 40 g of cooled concentrated solution. The cooled concentrated solution was treated in conformity with step 4 of Example 5 to obtain a precipitate by filtration. Next, 10 g of the acetone recovered in step 6 of Example 5 was added onto the precipitate cake, and the resultant substance was filtrated and washed, and then dried to obtain 1.00 g of dried substance. To this dried substance, 40 g of the ethanol recovered in step 6 of Example 5 was added, and the resultant substance was washed and dried in conformity with step 5 of Example 5 to obtain 0.72 g of dried substance washed with ethanol. Whereas the contents of astaxanthin and carotenoid in the substance dried at reduced pressure but before being washed with ethanol were respectively 33% and 70%, the contents of astaxanthin and carotenoid in the dried substance washed with ethanol were respectively 46% and 97%.

From the above, it was confirmed that reuse of the recovered solvents presents no problem.

Example 7

Production of Highly Pure Carotenoid Containing Astaxanthin at a High Content—4

The steps of bacteria culturing, extraction, and concentration and deposit were performed as in steps 1 through 3 of Example 5, and about 80 g of the cooled concentrated solution obtained in step 3 was filtrated at reduced pressure in conformity with step 4 of Example 5 to obtain a precipitate cake containing carotenoid. 20 g of acetone was added onto the cake, and the resultant substance was filtrated and washed. Then, a part of the cake was sampled in order to check the content of carotenoid in the precipitate. The step of drying was omitted. Then, 80 g of ethanol was added onto the cake, and the resultant substance was further filtrated and washed. The cake obtained by the filtration and washing was dried at reduced pressure at 35° C. overnight to obtain 1.50 g of dried substance washed with ethanol. Whereas the contents of astaxanthin and carotenoid in the substance dried at reduced pressure but before being washed with ethanol were respectively 33% and 70%, the contents of astaxanthin and carotenoid in the dried substance washed with ethanol were respectively 46% and 97%.

From about 100 g (about 120 mL) of the filtrate obtained by filtration of the precipitate performed in conformity with step 4 of Example 5, 85 g of acetone was recovered. From about 80 g (about 100 mL) of the filtrate obtained in the step of washing with ethanol performed in conformity with step 5 of Example 5, 75 g of ethanol contaminated with a trace amount of acetone was recovered.

Example 8

Production of Highly Pure Carotenoid Containing Astaxanthin at a High Content using the Recovered Solvents—4

To 25 g of the dry bacterial cells used in Example 7, 1.1 kg of the removed solution (acetone) obtained in Example 7 was added, and the resultant substance was treated with extraction of carotenoid and filtration of the bacterial cells in conformity with step 2 of Example 5 to obtain 1.1 kg of extract solution. The extract solution was concentrated at reduced pressure in conformity with step 3 of Example 5 to obtain about 40 g of cooled concentrated solution. The cooled concentrated solution was treated in conformity with step 4 of Example 5 to obtain a precipitate by filtration. Next, 10 g of the acetone obtained in Example 7 was added onto the precipitate cake, and the resultant substance was filtrated and washed. The step of drying was omitted as in Example 7. 40 g of the ethanol recovered in Example 7 was added thereto, and the resultant substance was further filtrated and washed. The cake obtained by the filtration and washing was dried at reduced pressure at 35° C. overnight to obtain 0.73 g of dried substance washed with ethanol. Whereas the contents of astaxanthin and carotenoid in the substance dried at reduced pressure but before being washed with ethanol were respectively 34% and 71%, the contents of astaxanthin and carotenoid in the dried substance washed with ethanol were respectively 46% and 97%.

In Example 8, it was confirmed that even when ethanol contaminated with acetone recovered by distillation at reduced pressure is used, no reduction in the washing capability is recognized. However, considering that ethanol is recovered and reused a plurality of times, it is considered to be preferable to provide some means to filtrate the precipitate under such a condition that acetone remains in the precipitate at a minimum possible level, before the step of washing with ethanol.

Example 9

Production of Highly Pure Carotenoid Containing Astaxanthin at a High Content—5

The procedure was performed in the same manner as in Example 5 except that washing was conducted with acetone instead of ethanol. The contents of astaxanthin and carotenoid in the obtained dried substance were respectively 45% and 91%.

Reference Example 1

Measurement of the Concentration of Astaxanthin Dissolved at Room Temperature

The concentration of astaxanthin (produced by Sigma) dissolved at room temperature was measured and shown in Table 1.

TABLE 1

| Type | Solvent | Concentration % (wt./wt.) |
|---|---|---|
| Hydrocarbons | Hexane | 0.003 |
|  | Cyclohexane | 0.001 |
|  | Toluene | 0.03 |
|  | Benzene | 0.05 |
| Alcohols | Methanol | 0.003 |
|  | Ethanol | 0.002 |
|  | Isopropanol | 0.002 |
| Ketones | Acetone | 0.02 |
|  | Methylethylketone | 0.03 |
|  | Methylisobutylketone | 0.02 |
|  | Cyclohexanone | 0.2 |
| Ethers | 1,4-dioxane | 0.3 |
|  | Tetrahydrofuran | 0.7 |
| Halogens | Dichloromethane | 2.3 |
|  | Chloroform | 0.7 |

As is clear from Table 1, it was found that the concentration dissolved in solvents other than halogen solvents having carcinogenicity or mutagenicity is as low as 1% or less. From this, it was revealed that as long as a general organic solvent having a relatively low level of hazardousness in liquid-liquid distribution of the conventional art is used, it is very difficult to realize high level purification using a solution having a carotenoid concentration exceeding 1%. This is a serious problem for industrial production.

The method of the present invention uses solidification/washing of solid, instead of liquid-liquid distribution. When a safely usable solvent which dissolves a concentration of only 1% or less is used, the conventional method needs to use a large amount of diluted solution for solution separation and thus requires very large facilities and is inefficient. By contrast, the method of the present invention can be carried out in a small scale.

Comparative Example 1

Production Method in Conformity with Example 1-1 of Japanese Laid-Open Patent Publication No. H 8-253695

To 2.3 kg (2.9 L) of extract solution obtained in substantially the same manner as in steps 1 to 2 of Example 5, which has an astaxanthin concentration of 0.034% (wt./wt.) and a carotenoid concentration of 0.077% (wt./wt.), 1.9 kg (2.9 L) of hexane and 2.9 kg (2.9 L) of 1% saline solution were added, and the resultant substance was stirred for 1 hour. After being left still, the resultant substance was separated into two layers to obtain 3.7 L (2.5 kg) of upper hexane layer and 5 L (4.6 kg) of lower water layer. The obtained hexane layer was concentrated at reduced pressure by an evaporator to prepare about 0.3 L of concentrated solution. After the concentrated solution was left at 4° C. for 12 hours, the precipitate was filtrated at reduced pressure. 25 mL of hexane was added onto the precipitate, and the resultant substance was filtrated and washed, and then dried at reduced pressure overnight to obtain 1.45 g of dried substance having an astaxanthin content of 47% and a carotenoid content of 98%.

Regarding the conditions of carotenoid purification, for example, in Example 5, about 1.8% (wt./wt.) of carotenoid suspension was sufficient; whereas in Comparative example 1, it was necessary to contact 5 L of water layer to 3.7 L of hexane solution having a carotenoid concentration as low as about 0.07% (wt./wt.). From this, it was found that the present invention is more efficient industrially than the method of Comparative example 1.

Also regarding the total amount of the solutions, the total volume of acetone and ethanol used in, for example, Example 5 was 2.925 L, whereas the total volume of acetone, hexane and 1% saline solution used in Comparative example 1 was 8.725 L. The amount of the solutions used in the steps of Comparative example 1 was about 3 times larger. Thus, it was found that the method of the present invention is more efficient industrially.

From about 2.9 L of the acetone used for the extraction, about 2.8 L was recovered in, for example, Examples 5 and 7 as the removed solution at the same time as when the extract solution was concentrated at reduced pressure during the production. By contrast, Comparative example 1 required an operation of recovering acetone and hexane by newly performing fractionation from about 3.4 L of the removed solution of acetone and hexane which was obtained by concentrating the hexane layer at reduced pressure, and also an operation of newly recovering acetone from about 5 L of water layer. From this, it was found that the method of the present invention can recover the solvent more easily.

Food Example 3

Margarine

The astaxanthin composition obtained in Example 5 was added as an antioxidant and coloring agent to vegetable oil such that the astaxanthin composition would be contained at 5% by weight of margarine. The resultant substance was stirred together with an emulsifier and the like so as to be uniform, and margarine was produced by a usual method. As compared with usual margarine, the obtained margarine exhibited a pale red color because of the presence of astaxanthin.

Food Example 4

Artificial Salmon Roe

The astaxanthin composition obtained in Example 5 was added to a 1% aqueous solution of sodium alginate at a ratio of 0.6%, and dispersed by a homogenizer. The resultant substance was dropped to a 5% aqueous solution of calcium chloride as a coagulator and molded into spheres having a diameter of 5 mm The spheres had a close-to-natural external appearance, and were very similar to salmon roe in terms of the shape, color and taste.

Formulation Example 3

Astaxanthin-Containing Tablet

To 120 parts by weight of the carotenoid-containing composition obtained in Example 5, 330 parts by weight of crystalline cellulose, 15 parts by weight of carmellose-calcium, 10 parts by weight of hydroxypropyl cellulose and 60 parts by weight of purified water were mixed in a usual method, and the resultant substance was dried. Then, 10 parts by weight of magnesium stearate was added thereto, and the resultant substance was tableted to obtain 100 mg of tablets containing a carotenoid-containing composition at a ratio of 20 mg/piece.

Formulation Example 4

Astaxanthin-Containing Soft Capsule

One part by weight of the carotenoid-containing composition obtained in Example 5 was suspended in soybean oil of a part by weight 5 times larger, and the resultant substance was sufficiently mixed so as to be uniform. Then, the resultant substance was filled into capsules by a capsule filler to obtain reddish brown capsules each containing 300 mg.

Cosmetic Example

Astaxanthin-Containing Cream (Cosmetic Substance)

The astaxanthin-containing composition obtained in Example 5 was added to white petrolatum so as to be contained at a ratio of 10% by weight, and the resultant substance was stirred together with an aromatic and the like so as to be uniform. Then, cream was produced by a usual method.

The present invention can provide a composition containing a high content of naturally-occurring, highly pure, low-cost and safe carotenoid, and a method for industrially producing the same. Hence, the present invention can also provide functional food, a pharmaceutical composition and a cosmetic substance comprising such a composition.

Sequence Listing Free Text

SEQ ID NO: 1
Information on bacterial strain E-396 (FERM BP-4283):
n is a, c, g or t (position: 1350)

The invention claimed is:

1. A method for producing a carotenoid-containing composition, comprising the following steps:
performing extraction on a culture of a microorganism, a concentrate of the culture, or a dried substance thereof containing carotenoid with at least one selected from the group consisting of lower alcohols, water-containing lower alcohols, lower dialkylketones and ethers;
concentrating the obtained extract solution to obtain a precipitate; and
washing the precipitate with at least one selected from the group consisting of lower alcohols, water-containing lower alcohols, and lower dialkylketones.

2. The method according to claim 1, wherein
the extraction is performed with ethanol or acetone; and
the precipitate is washed with ethanol, water-containing ethanol or acetone.

3. The method according to claim 1, wherein
the extraction is performed with ethanol; and
the precipitate is washed with water-containing ethanol.

4. The method according to claim 1, wherein
the extraction is performed with acetone; and
the precipitate is washed with ethanol.

5. The method according to claim 1, wherein
the extraction is performed with acetone; and
the precipitate is washed with acetone.

6. The method according to claim 1, further comprising the following step:
further washing the precipitate with hexane.

7. The method according to claim 1, wherein the carotenoid-containing composition contains 80% or greater of carotenoid.

8. The method according to claim 1, wherein the carotenoid contains 40% or greater of astaxanthin.

9. The method according to claim 1, wherein a DNA base sequence of the microorganism corresponding to 16S ribosomal RNA is substantially homologous to the base sequence represented by SEQ ID NO: 1.

10. The method according to claim 1, wherein the microorganism is E-396 strain (FERM BP-4283) or a mutant thereof.

* * * * *

SEQUENCE LISTING

```
<160> NUMBER OF SEQ ID NOS: 1

<210> SEQ ID NO 1
<211> LENGTH: 1452
<212> TYPE: DNA
<213> ORGANISM: FERM BP-4283
<220> FEATURE:
<221> NAME/KEY: misc_feature
<222> LOCATION: (1350)..(1350)
<223> OTHER INFORMATION: n is a, c, g, or t

<400> SEQUENCE: 1
agtttgatcc tggctcagaa cgaacgctgg cggcaggctt aacacatgca agtcgagcga      60
gaccttcggg tctagcggcg gacgggtgag taacgcgtgg gaacgtgccc ttctctacgg     120
aatagccccg ggaaactggg agtaataccg tatacgccct ttgggggaaa gatttatcgg     180
```

```
agaaggatcg gcccgcgttg gattaggtag ttggtggggt aatggcccac caagccgacg      240
atccatagct ggtttgagag gatgatcagc cacactggga ctgagacacg gcccagactc      300
ctacgggagg cagcagtggg gaatcttaga caatgggggc aaccctgatc tagccatgcc      360
gcgtgagtga tgaaggcctt agggttgtaa agctctttca gctgggaaga taatgacggt      420
accagcagaa gaagccccgg ctaactccgt gccagcagcc gcggtaatac ggaggggct       480 agcgttgttc ggaattactg ggcgtaaagc gcacgtaggc ggactggaaa gtcagaggtg      540
aaatcccagg gctcaacctt ggaactgcct ttgaaactat cagtctggag ttcgagagag      600
gtgagtggaa ttccgagtgt agaggtgaaa ttcgtagata ttcggaggaa caccagtggc      660
gaaggcggct cactggctcg atactgacgc tgaggtgcga aagcgtgggg agcaaacagg      720
attagatacc ctggtagtcc acgccgtaaa cgatgaatgc cagacgtcgg caagcatgct      780
tgtcggtgtc acacctaacg gattaagcat tccgcctggg gagtacggtc gcaagattaa      840
aactcaaagg aattgacggg ggcccgcaca agcggtggag catgtggttt aattcgaagc      900
aacgcgcaga accttaccaa cccttgacat ggcaggaccg ctggagagat tcagctttct      960
cgtaagagac ctgcacacag gtgctgcatg gctgtcgtca gctcgtgtcg tgagatgttc     1020
ggttaagtcc ggcaacgagc gcaacccacg tccctagttg ccagcaattc agttgggaac     1080
tctatggaaa ctgccgatga taagtcggag gaaggtgtgg atgacgtcaa gtcctcatgg     1140
gccttacggg ttgggctaca cacgtgctac aatggtggtg acagtgggtt aatccccaaa     1200
agccatctca gttcggattg tcctctgcaa ctcgagggca tgaagttgga atcgctagta     1260
atcgcggaac agcatgccgc ggtgaatacg ttcccgggcc ttgtacacac cgcccgtcac     1320
accatgggag ttggttctac ccgacgacgn tgcgctaacc ttcgggggc aggcggccac      1380 ggtaggatca gcgactgggg tgaagtcgta acaaggtagc cgtaggggaa cctgcggctg     1440
gatcacctcc tt                                                         1452
```